United States Patent
Mackey et al.

(10) Patent No.: US 10,289,891 B2
(45) Date of Patent: May 14, 2019

(54) OPTICAL BIOMETRIC SENSOR HAVING DIFFRACTIVE OPTICAL ELEMENTS

(71) Applicant: Synaptics Incorporated, San Jose, CA (US)

(72) Inventors: Bob Lee Mackey, San Jose, CA (US); Richard Andrew Klenkler, San Jose, CA (US)

(73) Assignee: Synaptics Incorpated, San Jose, CA (US)

( * ) Notice: Subject to any disclaimer, the term of this patent is extended or adjusted under 35 U.S.C. 154(b) by 431 days.

(21) Appl. No.: 15/086,951

(22) Filed: Mar. 31, 2016

(65) Prior Publication Data

US 2017/0286742 A1    Oct. 5, 2017

(51) Int. Cl.
*G06K 9/00*      (2006.01)
*G02B 27/42*     (2006.01)
*G02B 5/18*      (2006.01)
*G02B 27/30*     (2006.01)
*A61B 5/1172*    (2016.01)

(52) U.S. Cl.
CPC ........ *G06K 9/00046* (2013.01); *A61B 5/1172* (2013.01); *G02B 5/188* (2013.01); *G02B 27/30* (2013.01); *G02B 27/4205* (2013.01); *G06K 9/0008* (2013.01)

(58) Field of Classification Search
CPC .......... G06K 9/0008; G06K 2009/0006; A61B 5/1172; G02B 27/30; G02B 27/4205
See application file for complete search history.

(56) References Cited

U.S. PATENT DOCUMENTS

| 4,385,831 | A | 5/1983 | Ruell | |
|---|---|---|---|---|
| 5,892,599 | A | 4/1999 | Bahuguna | |
| 6,665,427 | B1* | 12/2003 | Keagy | G06K 9/00046 382/124 |
| 6,750,955 | B1 | 6/2004 | Feng | |
| 7,787,110 | B2* | 8/2010 | Raguin | G06K 9/00046 356/71 |
| 9,818,017 | B2* | 11/2017 | Wu | G06K 9/00046 |
| 2008/0203276 | A1* | 8/2008 | Dowski | G02B 3/0056 250/208.1 |
| 2012/0321149 | A1* | 12/2012 | Carver | G06K 9/0004 382/124 |
| 2013/0088430 | A1* | 4/2013 | Lee | G06F 3/0304 345/158 |

(Continued)

OTHER PUBLICATIONS

Attwood, David. *Soft x-rays and extreme ultraviolet radiation: principles and applications.* Cambridge university press, 2007.

(Continued)

*Primary Examiner* — Utpal D Shah
(74) *Attorney, Agent, or Firm* — Leydig, Voit & Mayer, Ltd.

(57) ABSTRACT

An optical sensor for imaging a biometric object includes: a cover layer transparent to light reflected off the biometric object; an optical layer, disposed below the cover layer, having a plurality of diffractive optical elements; and a sensing layer, having a plurality of sensing elements disposed below the optical layer, each of the sensing elements being configured to detect light from the biometric object. The plurality of diffractive optical elements of the optical layer are configured to direct light from the biometric object to the plurality of sensing elements.

24 Claims, 13 Drawing Sheets

(56) References Cited

U.S. PATENT DOCUMENTS

| | | |
|---|---|---|
| 2015/0347813 A1 | 12/2015 | Tsen |
| 2016/0132712 A1* | 5/2016 | Yang .................... G06K 9/0002 348/77 |
| 2016/0224816 A1* | 8/2016 | Smith .................... G02B 27/58 |
| 2016/0247010 A1 | 8/2016 | Huang et al. |
| 2017/0062504 A1 | 3/2017 | Minixhofer et al. |
| 2017/0220844 A1* | 8/2017 | Jones .................... G06K 9/0053 |
| 2018/0068160 A1* | 3/2018 | Wu .................... G06K 9/00013 |
| 2018/0069048 A1* | 3/2018 | Wu .................... G02B 5/208 |

OTHER PUBLICATIONS

Jenkins, Francis A., and Harvey E. White. *Fundamentals of optics.* Tata McGraw-Hill Book Company Inc., 1957, pp. 353-361.
Arago Spot, http://en.wikipedia.org/wiki/Arago_spot, downloaded from internet Aug. 26, 2016.
Joo, Jae Young, et al. "Design and Fabrication of a Fingerprint Imager with Compact LED Illumination and Compact Imaging Optics." *Optics Express* vol. 18, No. 18, Aug. 30, 2010, pp. 18932-18944.

\* cited by examiner

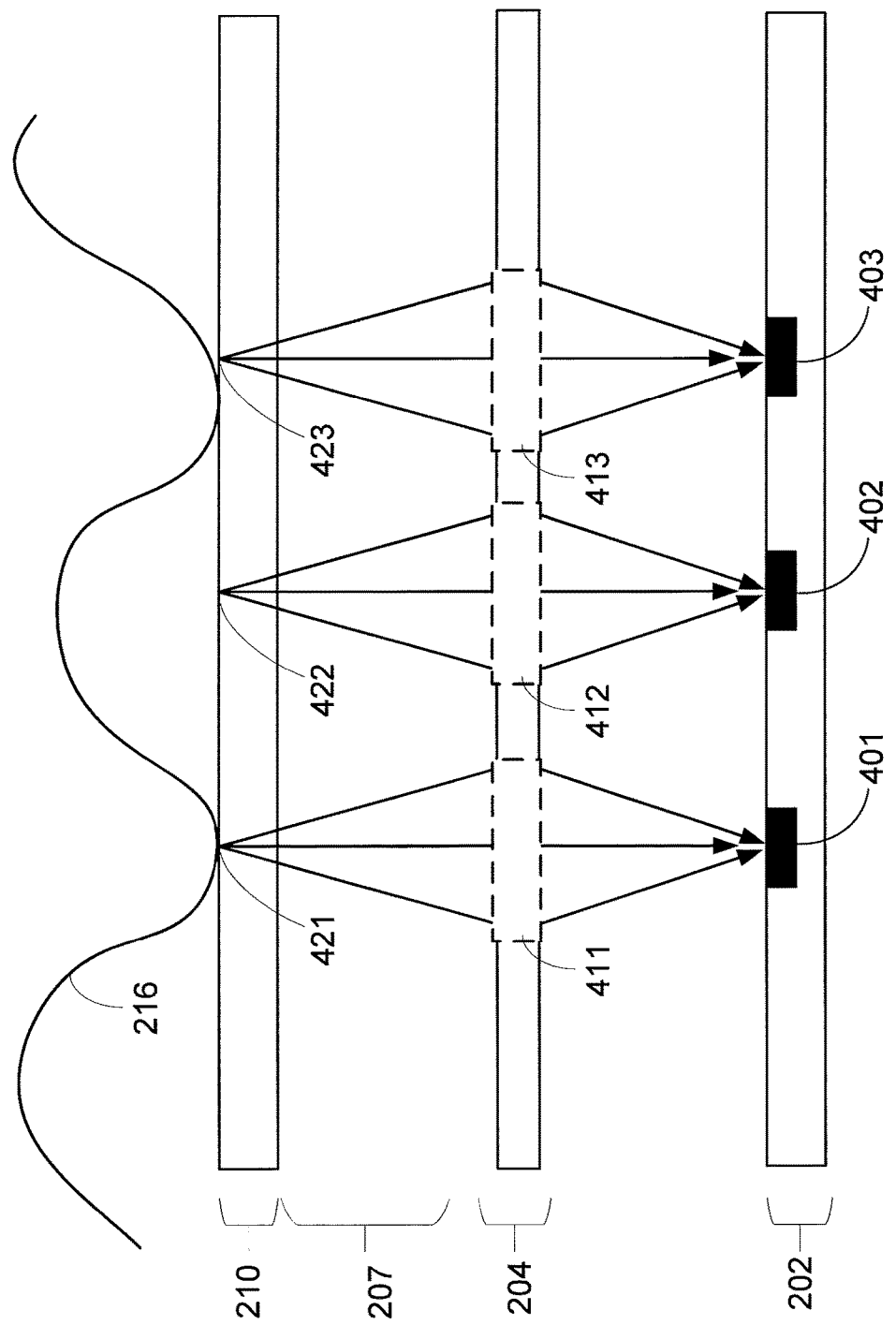

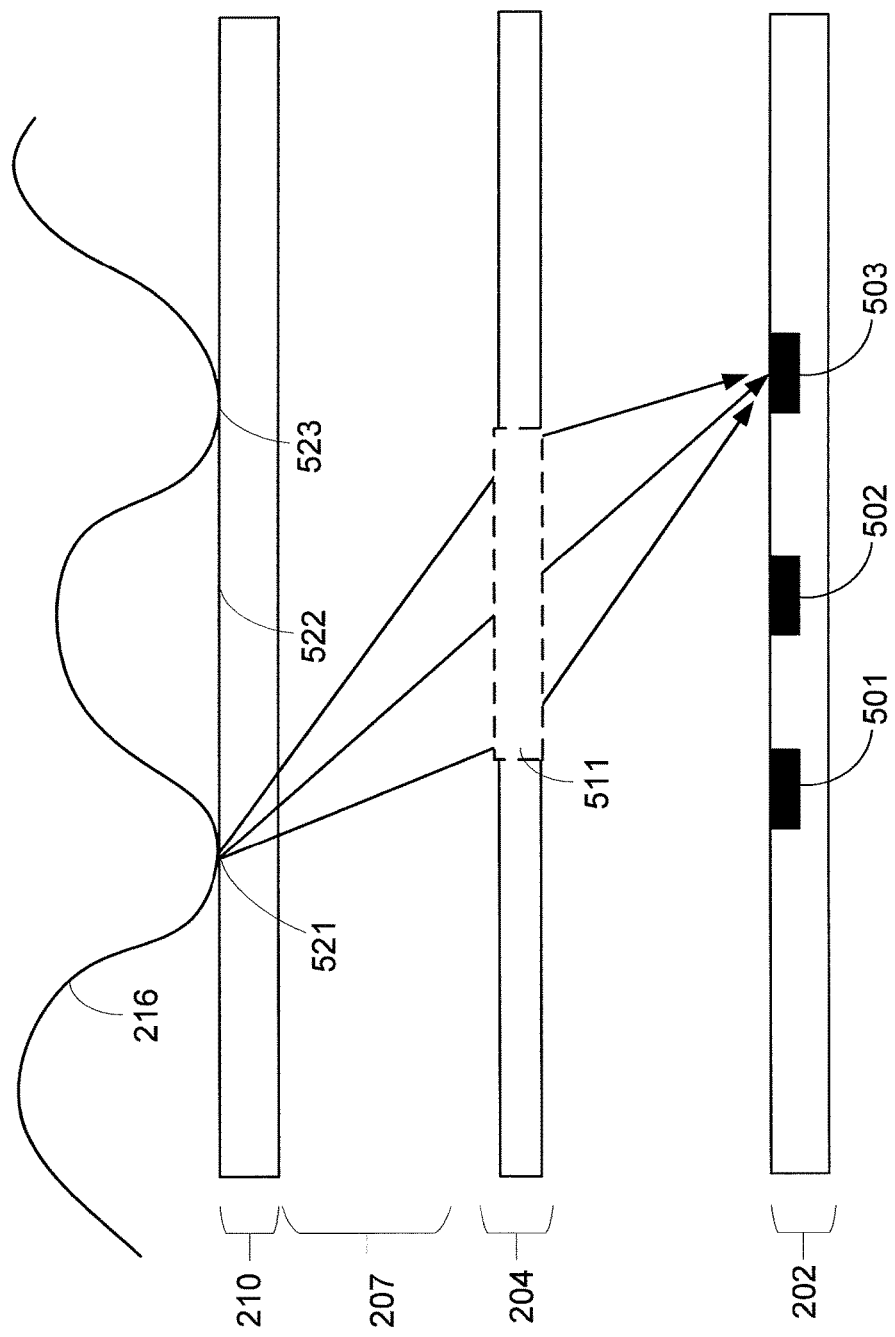

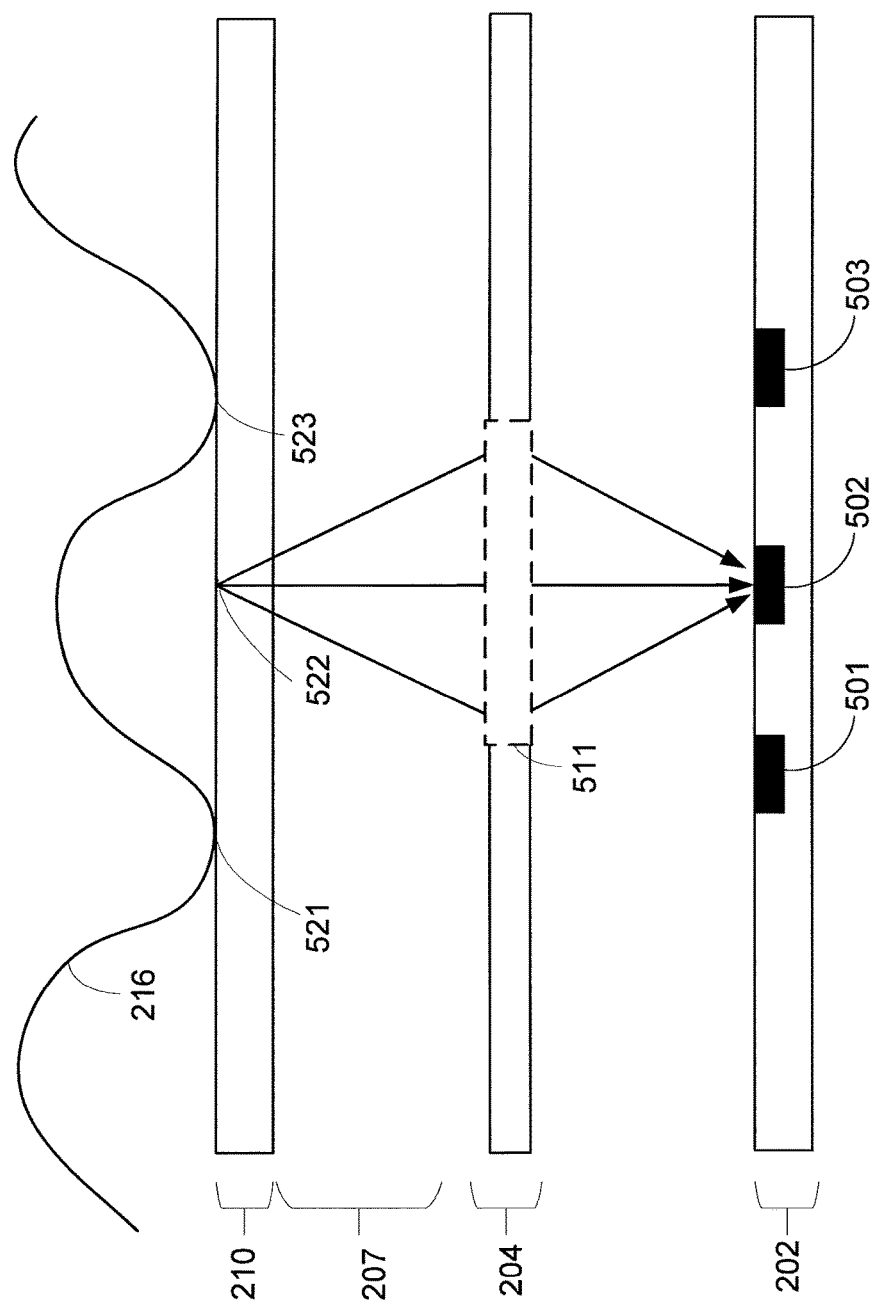

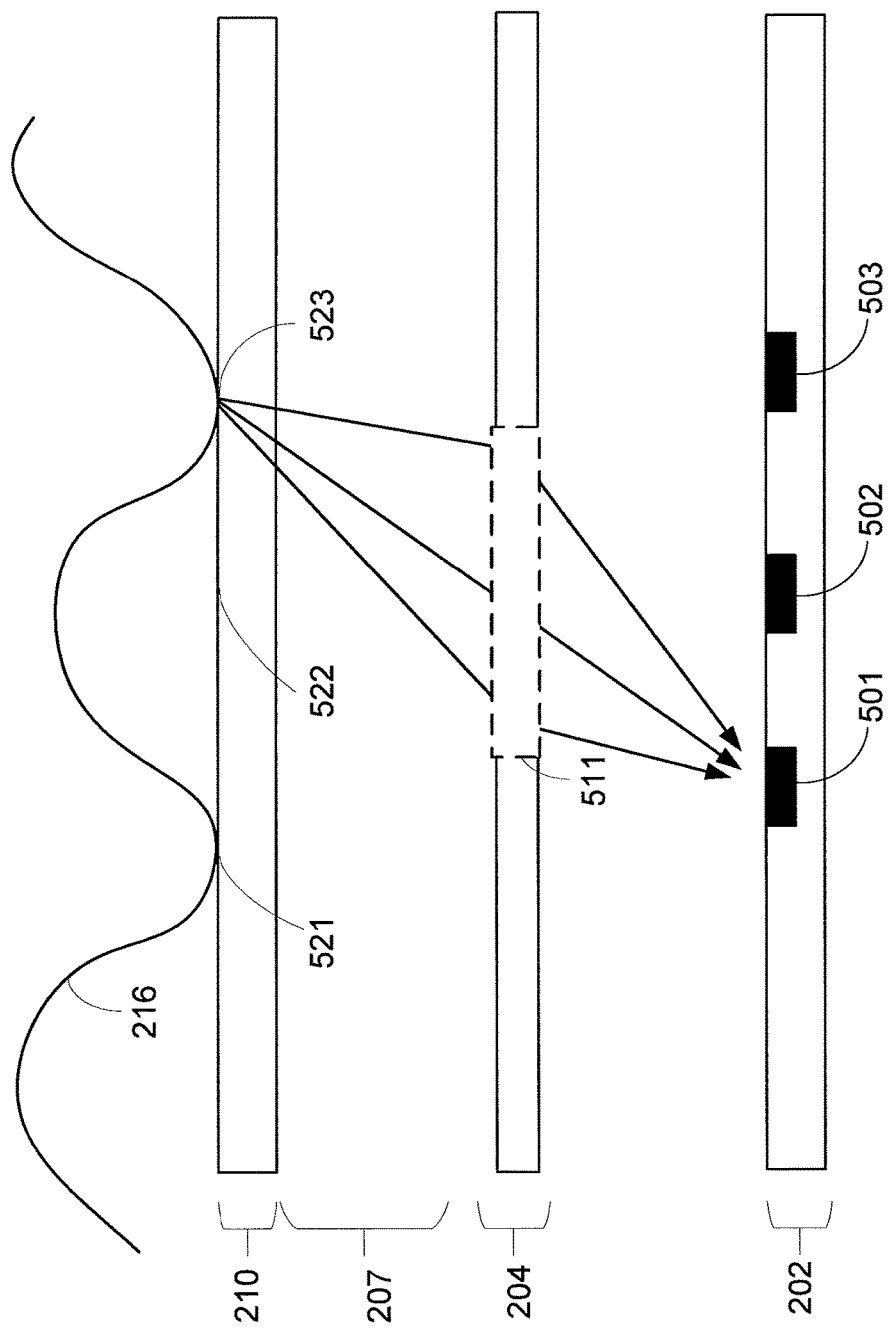

OPTICAL BIOMETRIC SENSOR HAVING DIFFRACTIVE OPTICAL ELEMENTS

FIELD

This disclosure generally relates to optical sensors, and more particularly to optical biometric sensors, such as fingerprint sensors, having diffractive optical elements.

BACKGROUND

Object imaging is useful in a variety of applications. By way of example, biometric recognition systems image biometric objects for authenticating and/or verifying users of devices incorporating the recognition systems. Biometric imaging provides a reliable, non-intrusive way to verify individual identity for recognition purposes. Various types of sensors may be used for biometric imaging.

Fingerprints, like various other biometric characteristics, are based on distinctive personal characteristics and provide a reliable mechanism to recognize an individual. Thus, fingerprint sensors have many potential applications. For example, fingerprint sensors may be used to provide access control in stationary applications, such as security checkpoints. Fingerprint sensors may also be used to provide access control in mobile devices, such as cell phones, wearable smart devices (e.g., smart watches and activity trackers), tablet computers, personal data assistants (PDAs), navigation devices, and portable gaming devices. Some applications (e.g., applications related to mobile devices) may require recognition systems that are both small in size and highly reliable.

Most commercially available fingerprint sensors are based on optical or capacitive sensing technologies. Conventional optical fingerprint sensors are typically too bulky to be packaged in mobile devices and other common consumer electronic devices, confining their use to door access control terminals and similar applications where sensor size is not a restriction.

As a result, fingerprint sensors in most mobile devices are capacitive sensors having a sensing array configured to sense ridge and valley features of a fingerprint. Typically, these fingerprint sensors either detect absolute capacitance (sometimes known as "self-capacitance") or trans-capacitance (sometimes known as "mutual capacitance"). In either case, capacitance at each sensing element in the array varies depending on whether a ridge or valley is present, and these variations are electrically detected to form an image of the fingerprint.

While capacitive fingerprint sensors provide certain advantages, commercially available capacitive fingerprint sensors typically have difficulty sensing fine ridge and valley features through large distances, requiring the fingerprint to contact a sensing surface that is close to the sensing array. It remains a significant challenge for a capacitive sensor to detect fingerprints through thick layers, such as the thick cover glass (sometimes referred to herein as a "cover lens") that protects the display of many smart phones and other mobile devices. To address this issue, a cutout is often formed in the cover glass in an area beside the display, and a discrete capacitive fingerprint sensor (often integrated with a mechanical button) is placed in the cutout area so that it can detect fingerprints without having to sense through the cover glass. The need for a cutout makes it difficult to form a flush surface on the face of device, detracting from the user experience and complicating the manufacture. The hole in the device enclosure also can allow moisture or contaminants to enter the device. The existence of mechanical buttons also takes up valuable device real estate.

SUMMARY

In an embodiment, an optical sensor for imaging a biometric object includes: a cover layer transparent to light reflected off the biometric object; an optical layer, disposed below the cover layer, having a plurality of diffractive optical elements; and a sensing layer, having a plurality of sensing elements disposed below the optical layer, each of the sensing elements being configured to detect light from the biometric object. The plurality of diffractive optical elements of the optical layer are configured to direct light from the biometric object to the plurality of sensing elements.

In an embodiment, an optical fingerprint sensor for imaging a fingerprint includes: a cover layer transparent to light reflected off the fingerprint; an optical layer, disposed below the optical layer, having a plurality of diffractive optical elements; and a sensing layer, having a plurality of sensing elements disposed below the optical layer, wherein each of the plurality of sensing elements are configured to detect light from the fingerprint. The plurality of diffractive optical elements of the optical layer are configured to direct light from the fingerprint to the plurality of sensing elements.

In an embodiment, a system for imaging a biometric object includes: an optical sensor and a processing system. The optical sensor includes: a cover layer transparent to light reflected off the biometric object; an optical layer, disposed below the cover layer, having a plurality of diffractive optical elements; and a sensing layer, having a plurality of sensing elements disposed below the optical layer. The plurality of diffractive optical elements of the optical layer are configured to direct light from the biometric object to the plurality of sensing elements. The processing system is connected to the plurality of sensing elements and is configured to obtain image data from the plurality of sensing elements and compare the obtained image data to a reference template.

BRIEF DESCRIPTION OF THE DRAWINGS

Examples of embodiments will be described in even greater detail below based on the figures. The invention is not limited to these examples. All features described and/or illustrated herein can be used alone or combined in different combinations in various embodiments. Features and advantages of various embodiments will become apparent by reading the following detailed description with reference to the attached drawings, which illustrate the following:

FIG. 4 illustrates an exemplary optical sensor having a plurality of diffractive optical elements where light passing through each respective diffractive optical element is resolvable at only one sensing element.

FIGS. 5A-5C illustrate an exemplary optical sensor having a plurality of diffractive optical elements where light passing through each respective diffractive optical element is resolvable at multiple sensing elements.

DETAILED DESCRIPTION

The following detailed description is exemplary in nature and is not intended to limit the invention or the application and uses of the invention. Furthermore, there is no intention to be bound by any expressed or implied theory presented in the preceding technical field, background, summary, brief description of the drawings, or the following detailed description.

Turning to the drawings, and as described in greater detail herein, embodiments of the disclosure provide methods and systems to optically image an input biometric object such as a fingerprint. In particular, methods and systems are described wherein an optical sensor includes an optical layer having a plurality of diffractive optical elements (e.g., an array of binary zone plates, photon sieves, Fresnel lens and/or sinusoidal zone plates), which operates as a light conditioning layer, interposed between a cover layer and an image sensor array having a plurality of optical sensing elements. Transmitted light from an illumination source is reflected from the input biometric object and passes through the cover layer. The reflected light is conditioned by the optical layer such that only a subset of the reflected light beams are resolved at the optical sensing elements in the image sensor array.

Employing the optical layer of the present disclosure prevents blurring while allowing for a biometric image sensor that has a lower profile than is possible with conventional optical and capacitive imaging sensors, and provides compatibility with a large range of thicknesses of cover layers. Thus, embodiments of the biometric image sensor discussed in the present disclosure are particularly suitable for applications where a thin sensor is desirable and where a relatively thick cover layer may be desirable, such as in mobile devices. Additionally, use of diffractive optical elements in the optical layer provides for relatively high efficiency, as the optical layer allows a large percentage of the reflected light beams to reach the sensing elements of the image sensor array.

Figure 1:
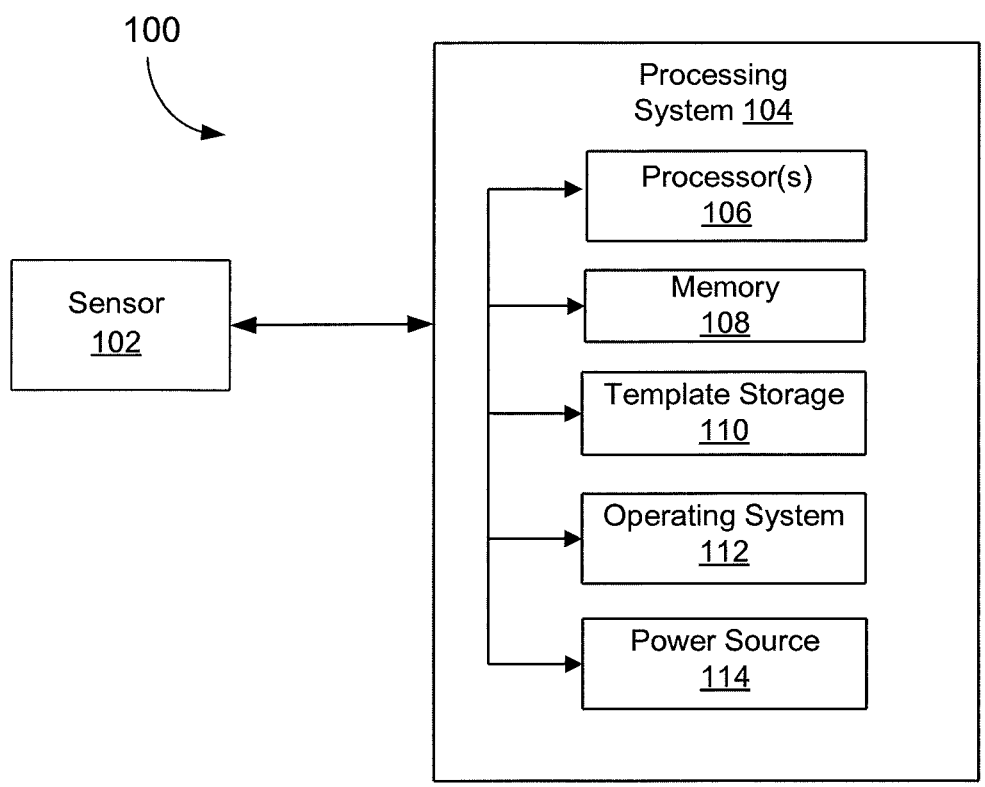
FIG. 1 is a block diagram of an exemplary system that includes an optical sensor and a processing system.

FIG. 1 is a block diagram of an exemplary system 100 that includes an optical sensor 102 and a processing system 104. Exemplary components of an electronic device utilized during capturing, storing, and/or validating a biometric match attempt are illustrated. The processing system 104 includes processor(s) 106, a memory 108, a template storage 110, an operating system (OS) 112, and a power source 114. Each of the processor(s) 106, the memory 108, the template storage 110, and the operating system 112 are interconnected physically, communicatively, and/or operatively for inter-component communications. The power source 114 is interconnected to the various system components to provide electrical power as necessary.

As illustrated, processor(s) 106 are configured to implement functionality and/or process instructions for execution for the system 100. For example, processor(s) 106 execute instructions stored in memory 108 to identify a biometric object or determine whether a biometric authentication attempt is successful or unsuccessful. Memory 108, which may be a non-transitory, computer-readable storage medium, is configured to store information and/or processor-executable instructions. In some embodiments, memory 108 includes a temporary memory, an area for information not to be maintained when the electronic device is turned off. Examples of such temporary memory include volatile memories such as random access memories (RAM), dynamic random access memories (DRAM), and static random access memories (SRAM). Memory 108 also maintains program instructions for execution by the processor 106.

Template storage 110 comprises one or more non-transitory computer-readable storage media. In the context of an exemplary fingerprint sensor, the template storage 110 is configured to store enrollment views for fingerprint images for a user's fingerprint or other enrollment information. More generally, the template storage 110 may be used to store information about an object. The template storage 110 may further be configured for long-term storage of information. In some examples, the template storage 110 includes non-volatile storage elements. Non-limiting examples of non-volatile storage elements include magnetic hard discs, solid-state drives (SSD), optical discs, floppy discs, flash memories, or forms of electrically programmable memories (EPROM) or electrically erasable and programmable (EEPROM) memories, among others.

The processing system 104 also hosts an operating system (OS) 112. The operating system 112 controls operations of the components of the processing system 104. For example, the operating system 112 facilitates the interaction of the processor(s) 106, memory 108 and template storage 110.

According to various embodiments, the processor(s) 106 implement hardware and/or software to obtain data describing an image of an input object. The processor(s) 106 may also align two images and compare the aligned images to one another to determine whether there is a match. The processor(s) 106 may also operate to reconstruct a larger image from a series of smaller partial images or sub-images, such as fingerprint images when multiple partial fingerprint images are collected during a biometric process, such as an enrollment or matching process for verification or identification.

The processing system 104 includes one or more power sources 114 to provide power to the electronic device 100. Non-limiting examples of power source 114 include single-use power sources, rechargeable power sources, and/or power sources developed from nickel-cadmium, lithium-ion, or other suitable material as well power cords and/or adapters which are in turn connected to electrical power.

Optical sensor 102 can be implemented as a physical part of the same device as the processing system 104, or can be physically separate from the processing system 104. As appropriate, the optical sensor 102 may communicate with parts of the electronic system 104 using any one or more of the following: buses, networks, and other wired or wireless interconnections. In some embodiments, optical sensor 102 is implemented as a fingerprint sensor to capture a fingerprint image of a user. In accordance with the disclosure, the optical sensor 102 uses optical sensing for the purpose of object imaging including imaging biometrics such as fingerprints. The optical sensor 102 can be incorporated as part of a display, for example, or may be a discrete sensor.

Some non-limiting examples of electronic systems 100 include personal computers of all sizes and shapes, such as desktop computers, laptop computers, netbook computers, tablets, web browsers, e-book readers, and personal digital assistants (PDAs). Additional example electronic systems 100 include composite input devices, such as physical keyboards and separate joysticks or key switches. Further example electronic systems 100 include peripherals such as data input devices (including remote controls and mice) and data output devices (including display screens and printers). Other examples include remote terminals, kiosks, video game machines (e.g., video game consoles, portable gaming devices, and the like), communication devices (including cellular phones, such as smart phones), and media devices (including recorders, editors, and players such as televisions, set-top boxes, music players, digital photo frames, and digital cameras).

The optical sensor 102 may provide illumination to a sensing region. Reflections from the sensing region in the illumination wavelength(s) are detected to determine input information corresponding to the input object.

The optical sensor 102 may utilize principles of direct illumination of the input object, which may or may not be in contact with a sensing surface of the sensing region depending on the configuration. One or more light sources and/or light guiding structures may be used to direct light to the sensing region. When an input object is present, this light is reflected off the input object, and the reflections can be detected by optical sensing elements and used to determine information about the input object.

The optical sensor 102 may also utilize principles of internal reflection to detect input objects in contact with a sensing surface. One or more light sources may be used to direct light in a light guiding element at an angle at which it is internally reflected at the sensing surface of the sensing region, due to different refractive indices at opposing sides of the boundary defined by the sensing surface. Contact of the sensing surface by the input object causes the refractive index to change across this boundary, which alters the internal reflection characteristics at the sensing surface, causing light reflected from the input object to be weaker at portions where it is in contact with the sensing surface. Higher contrast signals can often be achieved if principles of frustrated total internal reflection (FTIR) are used to detect the input object. In such embodiments, the light may be directed to the sensing surface at an angle of incidence at which it is totally internally reflected, except where the input object is in contact with the sensing surface and causes the light to partially transmit across this interface. An example of this is presence of a finger introduced to an input surface defined by a glass to air interface. The higher refractive index of human skin compared to air causes light incident at the sensing surface at the critical angle of the interface to air to be partially transmitted through the finger, where it would otherwise be totally internally reflected at the glass to air interface. This optical response can be detected by the system and used to determine spatial information. In some embodiments, this can be used to image small scale fingerprint features, where the internal reflectivity of the incident light differs depending on whether a ridge or valley is in contact with that portion of the sensing surface.

Figure 2:
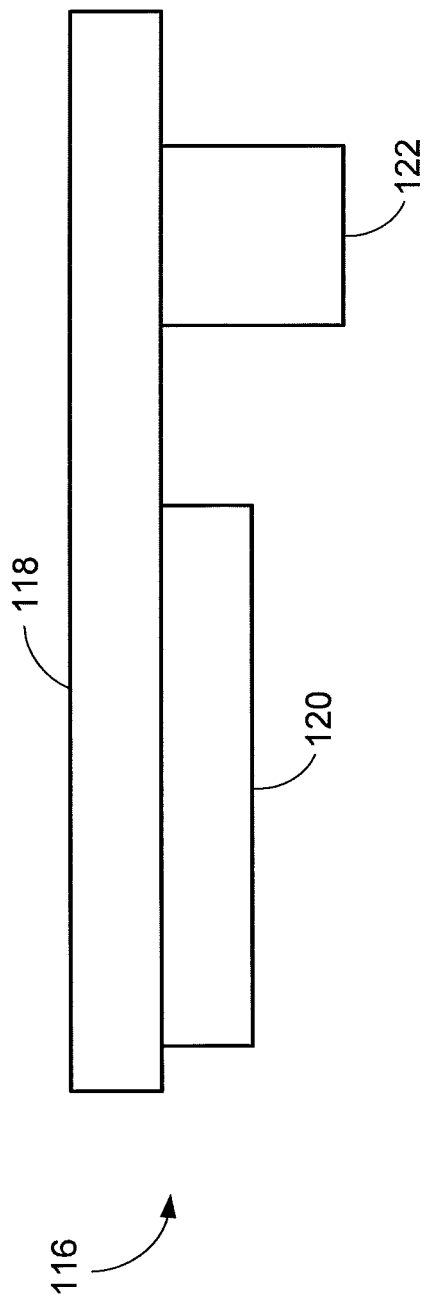
FIG. 2 illustrates an exemplary electronic device, such as a mobile phone, that includes an optical sensor.

FIG. 2 illustrates an exemplary electronic device 116, such as a mobile phone, that includes an optical sensor. The electronic device 116 includes cover glass 118 over a display 120. In certain embodiments, the optical sensor may be integrated with the display 120 (e.g., a portion of a touch screen display may provide a fingerprint sensing region). Alternatively, a discrete component 122 outside of the display active area may provide optical sensing capabilities.

Figure 3:
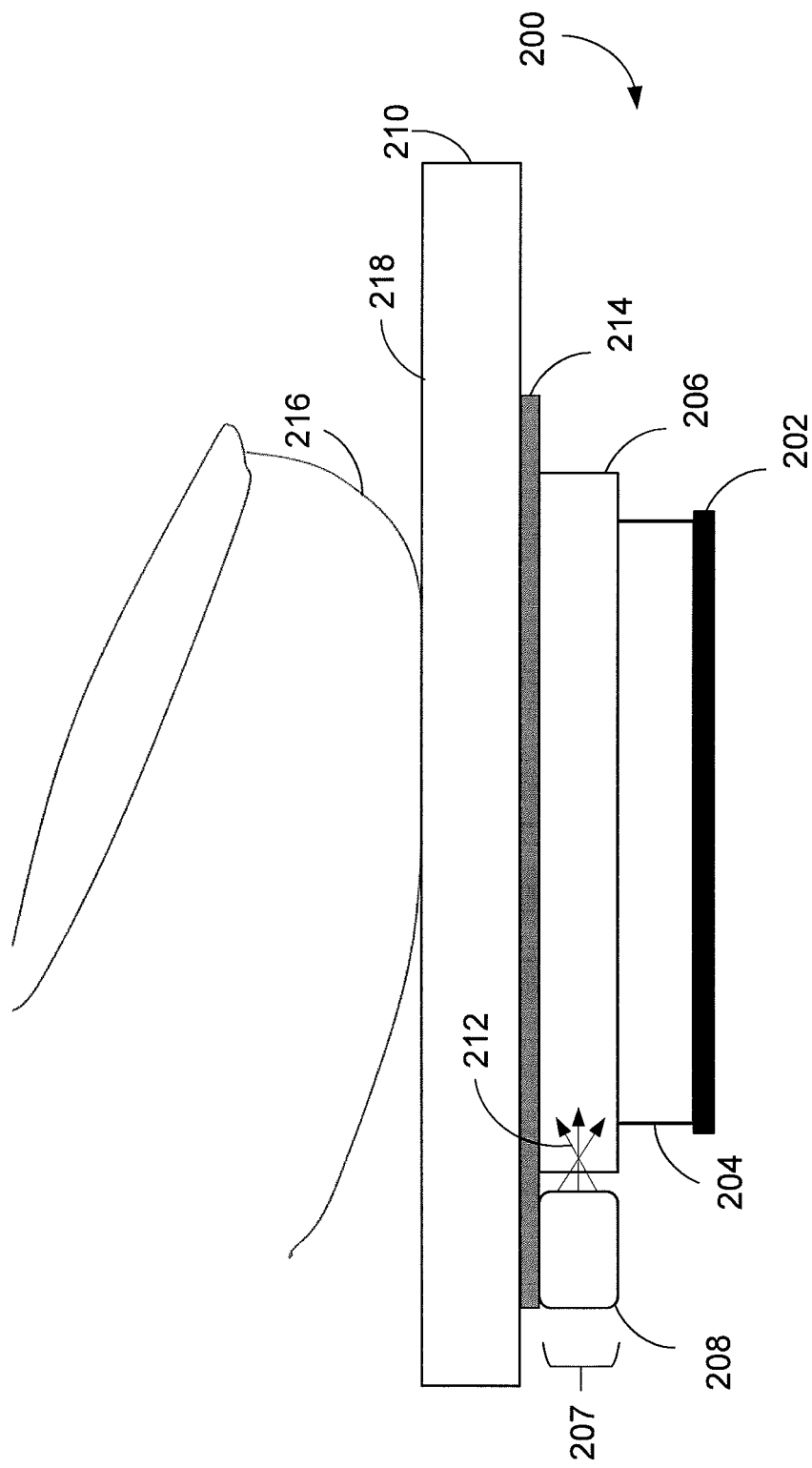
FIG. 3 illustrates an exemplary optical sensor having a layer of diffractive optical elements.

FIG. 3 illustrates an exemplary optical sensor having a layer of diffractive optical elements. The optical sensor 200 is used to image a biometric object 216, such as a fingerprint. The optical sensor 200 includes an image sensor array 202 having a plurality of sensing element or "pixels," an optical layer 204 disposed above the image sensor array 202 having a plurality of diffractive optical elements for conditioning light reflected off the biometric object, an illumination layer 207 disposed above the optical layer 204, a light source 208, and a cover layer 210. In certain embodiments, a blocking layer 214 may also be provided.

The cover layer 210 protects the inner components of the optical sensor 200 such as the image sensor array 202. The cover layer 210 may include a cover glass or cover lens that protects inner components of a display in addition to the optical sensor 200. A sensing region for the input object is defined above the cover layer 210. A top surface 218 of the cover layer 210 may form a sensing surface, which provides a contact area for the input object 216 (e.g., fingerprint). The cover layer 210 is made of any suitable material such as glass, transparent polymeric materials and the like.

Although generally described in the context of fingerprint for illustrative purposes, the input object 216 may be other biometric input objects as well. Generally, the input object 216 will have various features. By way of example, the biometric object 216 is a fingerprint that has ridges and valleys. Due to their protruding nature, the ridges contact the sensing surface 218 of the cover 210 layer. In contrast, the valleys do not contact the sensing surface 218 and instead form an air gap between the input object 216 and the sensing surface 218. The object 216 may have other features such as stain, ink and the like that do not create significant structural differences in portions of the input object 216, but which affect its optical properties. The methods and systems disclosed herein are suitable for imaging such structural and non-structural features of the input object 216.

The illumination layer 207 includes a light source 208 and/or a light guiding element 206 that directs illumination to the sensing region in order to image the input object. As shown in FIG. 3, the light source 208 transmits beams or rays of light 212 into the light guiding element 206, and the transmitted light propagates through the light guiding element 206. The light guiding element may utilize total internal reflection, or may include reflecting surfaces that extract light up towards the sensing region. Some of the light in the illumination layer may become incident at the sensing surface 218 in an area that is contact with the input object 216. The incident light is in turn reflected back towards the optical layer 204. In the example shown, the light source 208 is disposed adjacent to the light guiding element 206. However, it will be understood that the light source 208 may be positioned anywhere within the optical sensor 200 provided that emitted light reaches the light guiding element 206. For example, the light source 208 may be disposed below the image sensor array 202. Moreover, it will be understood that a separate light guiding element 206 is not required. For example, the light transmitted from the light source 208 can be transmitted directly into the cover layer 210 (the cover layer 210 may also serve as a light guiding element). As another example, the light transmitted from the light source 208 can be transmitted directly to the sensing region, in which case the light source 208 itself serves as the illumination layer.

A discrete light source is also not required. For example, the light provided by a display or the backlighting from an LCD may be suitable light sources (e.g., for mobile devices having touch screens). The light provided by the illumination layer 207 to image the object 216 may be in near infrared (NIR) or visible. The light can have a narrow band of wavelengths, a broad band of wavelengths, or operate in several bands.

The image sensor array 202 detects light passing through the optical layer 204. Examples of suitable sensor arrays are complementary metal oxide semiconductor (CMOS) and charge coupled device (CCD) sensor arrays. The image sensor array 202 includes a plurality of individual optical sensing elements (or "pixels") capable of detecting the intensity of incident light.

To achieve optical sensing of fingerprints and fingerprint-sized features through thicker cover layers 210, light reflected from the fingerprint is conditioned by the optical layer 204 so that the light reaching a sensing element in the image sensor array 202 comes from only a portion on the input object 216 directly above the sensor element. In the absence of such conditioning, any light arriving at a sensing element from a region on the object far away from the optical sensing elements contributes to image blurring.

In an exemplary implementation (as will be discussed below with respect to FIG. 4), each of the plurality of diffractive optical elements of the optical layer is configured such that light passing through the respective diffractive optical element is resolvable at only one sensing element of the plurality of sensing elements. In another exemplary implementation (as will be discussed below with respect to FIGS. 5A-5C), each of the plurality of diffractive optical elements of the optical layer is configured such that light passing through the respective diffractive optical element is resolvable at multiple sensing elements of the plurality of sensing elements.

To condition the light in accordance with the disclosure, the optical layer 204 is provided with an array of diffractive optical elements which are configured to generate constructive interference of light reflected off a fingerprint at each of the plurality of sensing elements. The constructive interference allows for light beams reflected off a particular portion of the fingerprint be resolved at each sensing element to provide corresponding pixel information at a respective sensing element, while light beams reflected off other portions of the fingerprint are not resolved at the respective sensing element. Examples of suitable diffractive optical elements that may be used include one or more binary zone plates, photon sieves, Fresnel lenses, and sinusoidal zone plates.

In one implementation, the optical layer may include a transparent substrate with an opaque patterned layer (e.g., the opaque patterned layer may be patterned with binary zone plates). In another exemplary implementation, the optical layer may include an opaque substrate with openings (e.g., the openings may be distributed in the form of photo sieves).

Also shown in FIG. 3 is blocking layer 214, which is optionally provided as part of optical sensor 200. The blocking layer 214 is a semitransparent or opaque layer that may be disposed above the optical layer 204. By way of example, the blocking layer may be disposed between the cover layer 210 and the illumination layer 207, as shown in FIG. 3. Alternatively, the blocking layer 214 may be disposed between the illumination layer 207 and the optical layer 204. In either case, the blocking layer 214 obscures components of the optical sensor 200, such as the diffractive optical elements of the optical layer, from ambient light illumination while still allowing the optical sensor 200 to operate.

The blocking layer 214 may include of a number of different materials or sub-layers. For example, a thin metal or electron conducting layer may be used where the layer thickness is less than the skin depth of light penetration in the visible spectrum. Alternately, the blocking layer 214 may include a dye and/or pigment or several dyes and/or pigments that absorb light, for example, in the visible spectrum. As yet another alternative, the blocking layer 214 may include several sub-layers or nano-sized features designed to cause interference with certain wavelengths, such as visible light for example, so as to selectively absorb or reflect different wavelengths of light. The light absorption profile of the blocking layer 214 may be formulated to give a particular appearance of color, texture, or reflective quality thereby allowing for particular aesthetic matching or contrasting with the device into which the optical sensor 200 is integrated. If visible illumination wavelengths are used, a semitransparent layer may be used to allow sufficient light to pass through the blocking layer to or from the sensing region, while still sufficiently obscuring components below.

FIG. 4 illustrates an exemplary optical sensor having a plurality of diffractive optical elements where light passing through each respective diffractive optical element is resolvable at only one sensing element. Specifically, each of the sensing elements 401, 402 and 403 is configured to detect the light intensity corresponding to a respective region above the cover layer 210 (regions 421, 422 and 423 in this example). Thus, diffractive optical element 411 causes constructive interference of light coming from region 421 at sensing element 401, diffractive optical element 412 causes constructive interference of light coming from region 422 at sensing element 402, and diffractive optical element 413 causes constructive interference of light coming from region 423 at sensing element 403, allowing for features of biometric object 216 (such as the depicted ridges and valleys of a fingerprint) to be detected.

Illustratively shown are exemplary light rays passing through the cover layer 210 which are directed by the diffractive optical elements 411, 412 and 413 to constructively interfere at the sensing elements 401, 402 and 403. For example, exemplary light rays reflecting off a ridge of the biometric object 216 at region 421 on top of the cover layer are directed by diffractive optical element 411 to constructively interfere at sensing element 401. The optical sensing element 401 can thus measure the intensity of light to provide data for the pixel corresponding to sensing element 401. Light rays that originate from other locations are not resolved at sensing element 401 due to the configuration of the optical layer, as light impinging on 411 from areas outside 421 are not focused onto 401. Instead, those rays may be diverted to the sensing layer 202 in areas between sensing elements, or reflected back towards the finger 216. The off-axis or "stray" light may also be directed to illuminate a large area in a non-specific way so that it forms a relatively harmless background for the image.

It will be appreciated that the ridges and valleys of biometric object 216 are merely illustrative and are not depicted to scale.

In certain embodiments, to increase resolution, the sampling density of the optical sensor should be large enough such that multiple samples are taken of each feature of interest. Thus, for example, to image ridges in a fingerprint, the distance between the sensing elements may be on the order of 50 to 100 microns since the width of the ridges themselves may be on the order of 150 to 250 microns. If it desired to capture smaller features, such as pores in a fingerprint, a smaller pitch such as 25 microns would be appropriate. Conversely, a larger pitch can be used to capture larger features of an input object.

In certain embodiments, to provide adequate mechanical strength, the glass cover lenses of certain handheld devices may have a thickness of 0.4 to 1.0 mm.

FIGS. 5A-5C illustrate an exemplary optical sensor having a plurality of diffractive optical elements where light passing through each respective diffractive optical element is resolvable at multiple sensing elements. Specifically, each of the sensing elements 501, 502 and 503 is configured to detect a light intensity corresponding to regions 523, 522 and 521 above the cover layer 210, respectively. Thus, diffractive optical element 511 simultaneously causes constructive interference of light coming from region 521 at sensing element 503 (see light beams depicted in FIG. 5A), constructive interference of light coming from region 522 at sensing element 502 (see light beams depicted in FIG. 5B), and constructive interference of light coming from region 523 at sensing element 501 (see light beams depicted in FIG. 5C), allowing for features of biometric object 216 (such as the depicted ridges and valleys of a fingerprint) to be detected.

In an example, each pixel may have a pitch size of 25 to 70 um. The cover glass may have a 0.4 to 1.0 mm thickness. The diffractive layer thickness may be extremely thin (<100 nm), or it may be thicker as well. The spacing from the diffractive layer to the sensor plane is related to cover glass thickness and the diffractive lens focal length (e.g., 1/f=1/L1+1/L2, where f=focal length, L1=lens-object plane thickness, L2=lens-image plane distance). In one example, the distance between the top of the cover glass and the sensing elements is between 0.2 and 2.0 mm.

It will be appreciated that, in the example depicted in FIGS. 5A-5C, each diffractive optical element in the optical layer corresponds to a 3×3 array of image sensing elements or pixels. In other exemplary embodiments, the configuration of the diffractive optical elements may be different such that a different correspondence is achieved (such as each diffractive element corresponding to a 2×2 array of pixels, a 4×4 array of pixels, etc.).

For embodiments where each of the diffractive optical elements corresponds to an N×N array of pixels (with N greater than 1), or an N×M array (with N and/or M greater than 1), each of the arrays of pixels produces an inverted subview of a particular view of the biometric object being imaged. In certain embodiments, the diffractive elements and the arrays of pixels may be positioned such that an array of pixels corresponding to one diffractive element overlaps with an array of pixels corresponding to another diffractive element (i.e., with light from multiple diffractive elements being resolvable at an individual sensing element).

Figure 6:
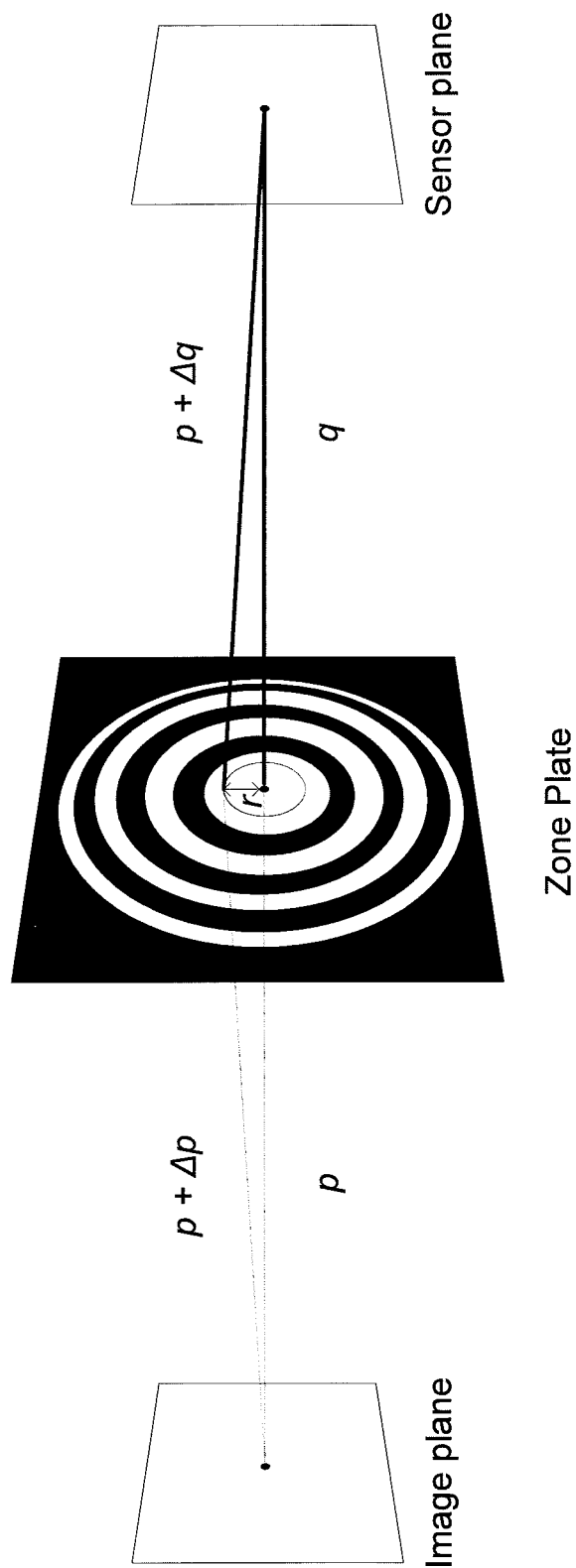
FIG. 6 illustrates an exemplary binary zone plate design that can be used for the diffractive optical elements of the optical layer in exemplary embodiments of the disclosure.

FIG. 6 illustrates an exemplary binary zone plate design that can be used for the diffractive optical elements of the optical layer in exemplary embodiments of the disclosure. In general, the ideal geometry for a zone plate is as follows:

$$r_n^2 = \frac{\frac{\left((n\lambda/2 + q + p)^2 - p^2 - q^2\right)^2}{4} - p^2 q^2}{(n\lambda/2 + q + p)^2}$$

where $r_n$ is the radius of the transition from the $n^{th}$ to the $n^{th}+1$ zone, n is zone number, p is the distance from the object to the zone plate, q is the distance from the zone plate to the sensor, and λ is the wavelength of illumination (see FIG. 6). The binary zone plate is designed to block light diffracted from either odd or even zones, so that light waves from the image plane (on top of the cover layer) arrive in phase at a sensing element on the sensor plane (and thus interfere constructively).

In an exemplary implementation, with an illumination light source with a wavelength centered on 550 nm, a distance p of 700 um (i.e., from the fingerprint to a binary zone plate), and a distance q of 700 um (i.e., from the binary zone plate to a sensing element), the zone plate geometry is as follows in the table below:

| Zone Index # | Zone Transition Diameter (μm) | Zone Width (μm) |
|---|---|---|
| 1 | 27.8 | 27.8 |
| 2 | 39.2 | 5.7 |
| 3 | 48.1 | 4.4 |
| 4 | 55.5 | 3.7 |
| 5 | 62.1 | 3.3 |
| 6 | 68.0 | 3.0 |
| 7 | 73.4 | 2.7 |
| 8 | 78.5 | 2.5 |
| 9 | 83.3 | 2.4 |
| 10 | 87.8 | 2.3 |
| 11 | 92.1 | 2.1 |
| 12 | 96.2 | 2.0 |
| 13 | 100.1 | 2.0 |
| 14 | 103.9 | 1.9 |
| 15 | 107.6 | 1.8 |
| Border | — | — |

In an example having a 50 um sensor pitch with a square grid, the zone indices greater than approximately the $7^{th}$ or $8^{th}$ zone indices would not be used because they would interfere with adjacent pixels.

Figure 7:
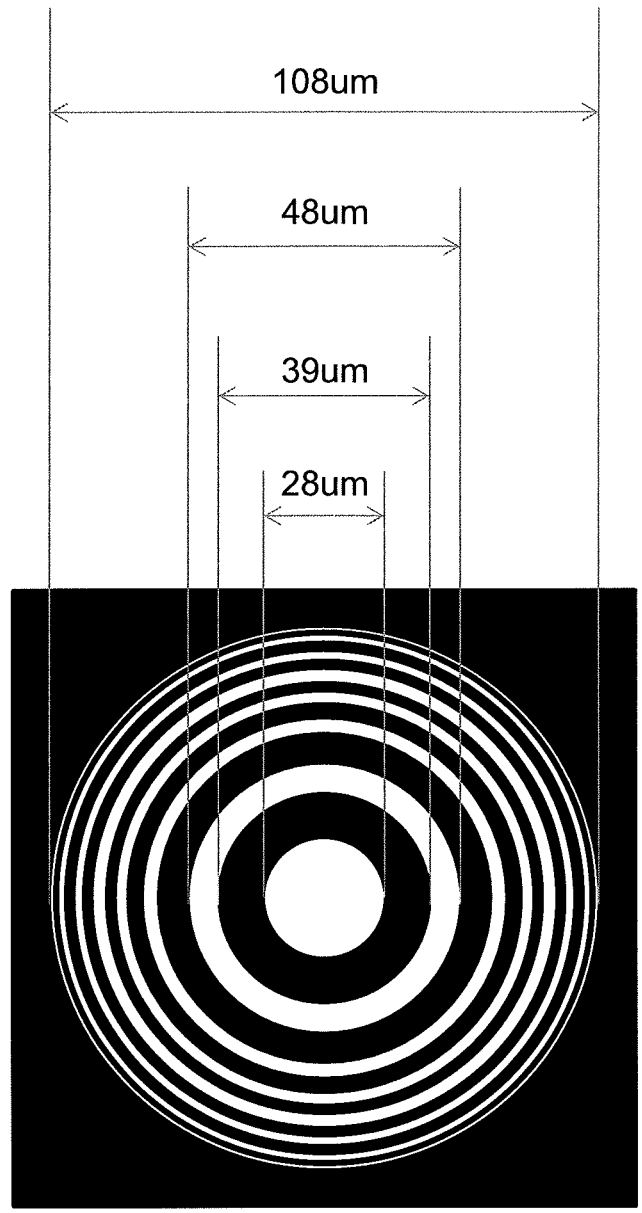
FIG. 7 illustrates an exemplary binary zone plate having an exemplary set of dimensions.

FIG. 7 illustrates an exemplary binary zone plate having the dimensions identified in the table above. Such a binary zone plate would provide a resolution of 2.2 μm (1.22× outer zone width). However, roughness or mis-registration of the features defining the zones would limit this resolution, and ideally, edge roughness should be <10% of the width of the outer (finest featured) zone.

Figure 8:
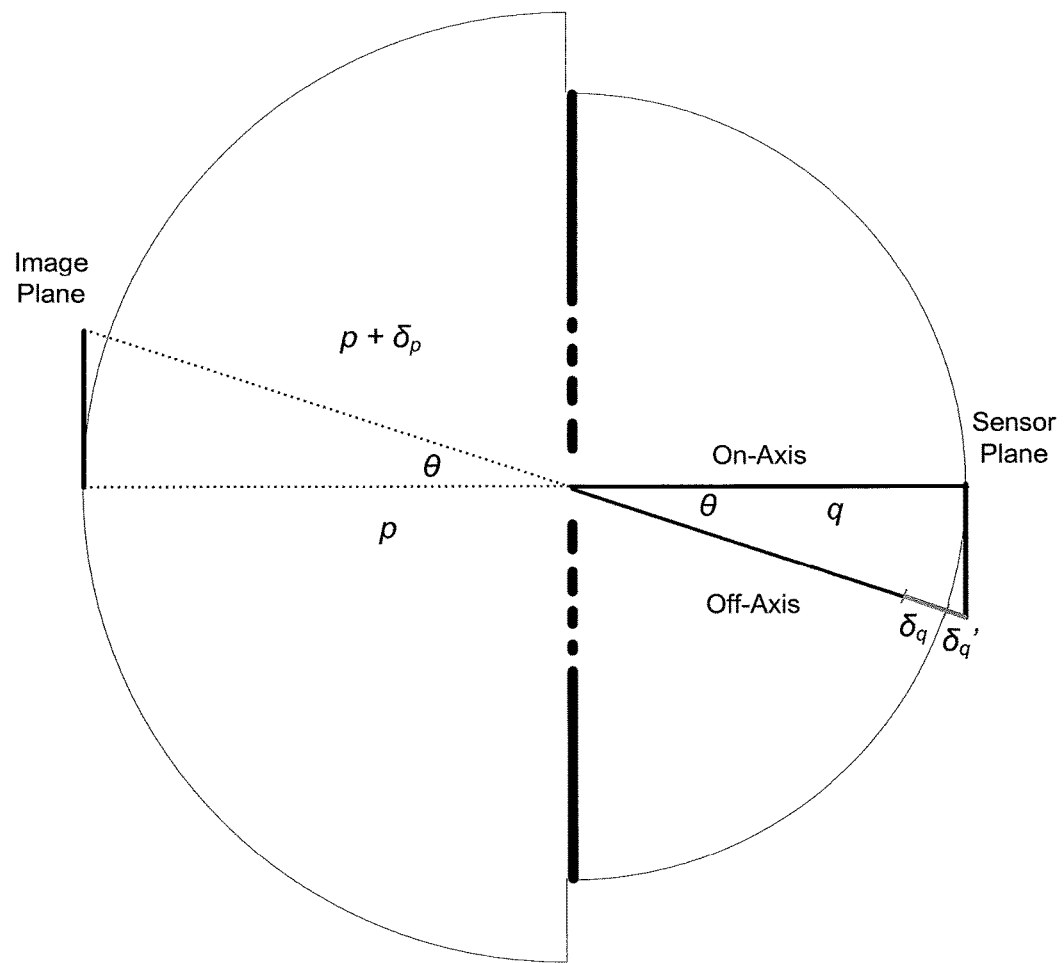
FIG. 8 illustrates an exemplary on-axis light ray and an exemplary off-axis light ray in an exemplary zone plate-based optical system.

For embodiments where a high degree of imaging fidelity is desired for sensing elements that are off-axis from the diffractive optical element (e.g., embodiments such as the one depicted in FIGS. 5A-5C where certain sensing elements are intended to detect features from the image plane that are not directly across from the respective sensing elements), further parameters relating to the field of view (FOV) are considered. For zone plate-based optical systems, FOV is often expressed as a maximum angular size over which the system exhibits good performance. As illustrated in FIG. 8, an off-axis light ray arrives at the sensor plane slightly out of phase from the on-axis light ray. The FOV of such a system is thus limited by the zone plate's depth of focus (DOF).

In order for the imaging fidelity to remain high at the angular field point θ, δq+δ'q should be less than the image-side DOF of the system ($\lambda/NA_i^2$). Satisfying this criterion leads to one quarter wave of defocus at the angular field point θ. If better wavefront quality is desired, a stricter criterion should be met—for example, a wavefront quality of λ/10 is achieved when δq+δ'q is less than DOF/2.5. The angular field point θ for a particular wavefront quality can be expressed as follows:

$$\theta = 2\left(\frac{\lambda}{\eta NA_i^2} \frac{1}{q+m^2 p} + 1\right)^2 - 2$$

where $\eta$ is a scaling factor ($\delta q + \delta' q < DOF/\eta$).

The foregoing equations relating field of view are also applicable with respect to the acceptance angle of the exemplary embodiment of FIG. 4 and the exemplary binary zone plates illustrated in FIGS. 6-7, where light passing through each respective diffractive optical element is resolvable at one only sensing element. For the exemplary dimensions discussed above with respect to FIG. 7, $\theta=8.2°$ for a wavefront quality of $\lambda/10$, which corresponds to an imaging spot on the fingerprint of ~200 μm diameter. With these restrictions, the zone plate behaves like a collimator given that the outer diameter of the zone plate is 108 um.

Figure 9:
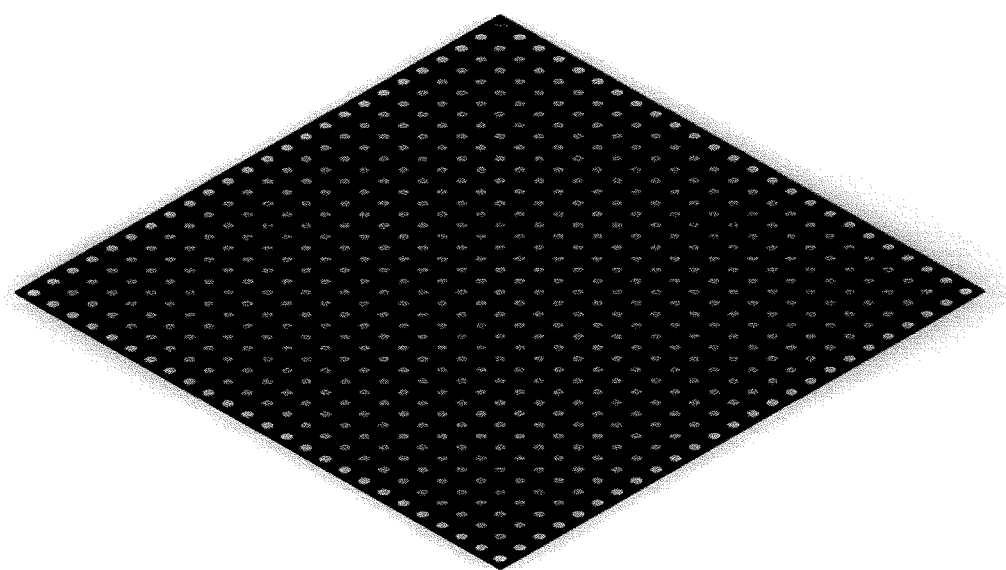
FIG. 9 illustrates an exemplary array of diffractive optical elements for focusing an exemplary 5×5 mm image onto an exemplary 5×5 mm sensor array.

For imaging an exemplary fingerprint in a 5×5 mm area, an array of the zone plates discussed above with respect to FIG. 7 may be utilized, with each zone plate focusing a 200 μm diameter region of the fingerprint onto a 5×5 mm sensor array. Thus, with this zone plate geometry, a 25×25 array of zone plates is utilized to focus a 5×5 mm image onto a 5×5 mm sensor array. Further, where the illumination light source has a wavelength centered on 550 nm, the distance from the fingerprint to the zone plate is 700 μm, and the distance from the zone plate to sensor is 700 μm. FIG. 9 illustrates an exemplary array of diffractive optical elements for focusing the exemplary 5×5 mm image onto the exemplary 5×5 mm sensor array.

In an alternative embodiment, photon sieve-type diffractive optical elements may be used instead of binary zone plate diffractive optical elements. Advantages of using the photon sieve-type diffractive optical elements may include improvements in resolution, limiting distortion from higher order diffraction, and lowering illumination light chromatic aberration. Manufacture of photon sieve-type diffractive optical elements may be carried out in a manner similar to processes for making a binary zone plate diffractive optical elements.

In another alternative embodiment, sinusoidal zone plates may be used as the diffractive optical elements to limit distortions from higher order diffraction.

Figure 11:
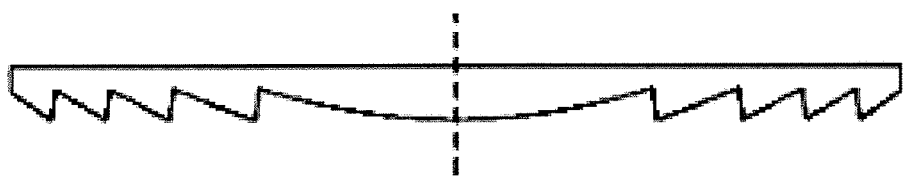
FIG. 11 illustrates an example of a Fresnel lens patterned from a transparent material.

In yet another alternative embodiment, Fresnel lenses may be used as the diffractive optical elements. A Fresnel lens can be produced, for example, by stamping, molding, or imprinting a pattern into a transparent material. FIG. 11 illustrates an example of a Fresnel lens patterned from a transparent material.

Figure 10:
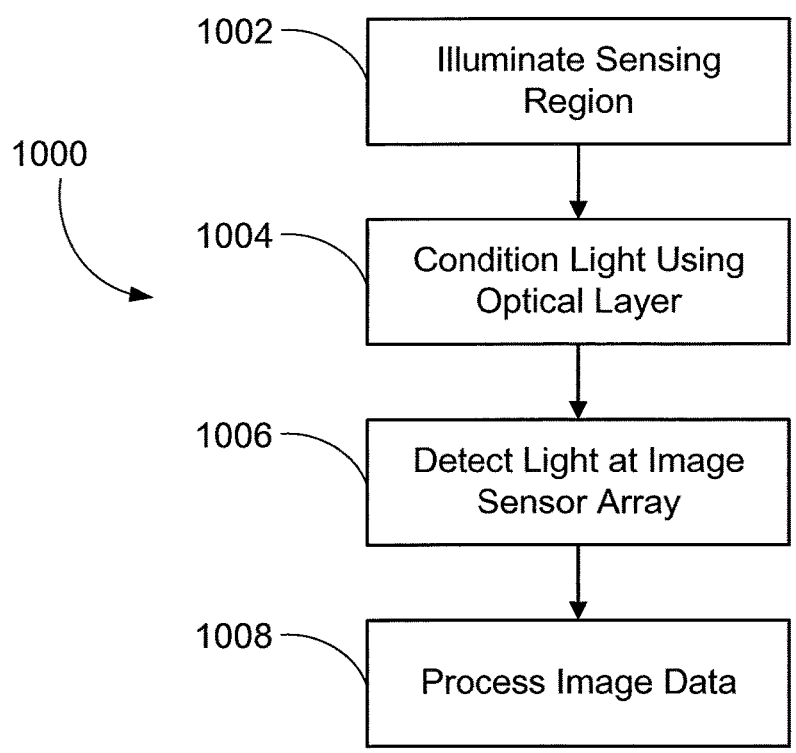
FIG. 10 illustrates an exemplary method for imaging an input biometric object.

FIG. 10 shows a method 1000 of imaging an input biometric object in accordance with the present disclosure. At stage 1002, the sensing region is illuminated using an illumination layer having a light source and/or light guiding element. As previously described, this may be done by using a light source directing light into a separate light guiding element or by transmitting light directly into a cover layer. The transmitted light is directed towards a sensing region above the cover layer and reflected from the object towards an optical layer.

At stage 1004, diffractive optical elements of the optical layer condition the light and direct it towards the sensing elements of an image sensor array (or "sensing layer").

At stage 1006, light which constructively interferes at the sensing elements of the image sensor array is detected at the sensing elements of the image sensor array.

At stage 1008, the detected light at the image sensor array is processed to form a view of the input object (which may be a full image or partial image of the input object). It will be appreciated that in embodiments where each diffractive optical element corresponds to an array of multiple pixels, each multiple-pixel array may capture an inverted subview, and additional processing may be utilized to stitch multiple inverted subviews together to form a view of the biometric object.

Further processing may also be performed on an obtained view of the biometric object, including, for example, stitching partial images together to form a template, and/or relating various partial images to one another in a template, and/or comparing captured image data to previously stored image data as part of an identification or verification process (e.g., to provide an authentication result based on comparing the obtained image data to a reference template). In one example, the processing system is configured to obtain image data from the plurality of sensing elements and compare the obtained image data to a reference template. In another example, the processing system is further configured to combine partial images corresponding to the image data into composite data before comparing the obtained image data to a reference template.

Although the foregoing examples generally describe optical imaging in the context of fingerprint image sensing, the methods and systems discussed herein may be used to image other types of objects as well. For example, a high resolution image of a palm or other biometric pattern may also be obtained in a similar manner.

It will be appreciated that embodiments of the invention achieve high levels of efficiency and achieving power savings, while allowing for optical sensing to be achieved within a thin amount of space, through the use of the diffractive optical elements in an optical layer as discussed herein. Further, for embodiments where restricting cross talk between neighboring optical sensing elements is desired, the diffractive optical elements may be configured to allow the reflected light to be resolved only at respective sensing elements.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An optical sensor for imaging a biometric object, the optical sensor comprising:
  a cover layer transparent to light reflected off the biometric object;
  an optical layer, disposed below the cover layer, having a plurality of diffractive optical elements; and
  a sensing layer, having a plurality of sensing elements disposed below the optical layer, each of the sensing elements being configured to detect light from the biometric object;
  wherein each of the plurality of diffractive optical elements of the optical layer is configured to diffract and direct light from the biometric object to one or more of the plurality of sensing elements;
  wherein the plurality of diffractive optical elements comprises one or more binary zone plates.

2. The optical sensor according to claim 1, wherein each of the plurality of diffractive optical elements of the optical layer is configured such that light passing through the respective diffractive optical element is resolvable at only one sensing element of the plurality of sensing elements.

3. The optical sensor according to claim 1, wherein each of the plurality of diffractive optical elements of the optical layer is configured such that light passing through the respective diffractive optical element is resolvable at multiple sensing elements of the plurality of sensing elements.

4. The optical sensor according to claim 1, wherein the optical layer comprises a transparent substrate with an opaque patterned layer.

5. The optical sensor according to claim 1, further comprising:
  a light source, configured to provide the light which is reflected off the biometric object.

6. The optical sensor according to claim 1, wherein the biometric object is a fingerprint, and each of the plurality of diffractive optical elements corresponds to a respective subview or pixel of the fingerprint.

7. The optical sensor according to claim 1, wherein the distance between a top surface of the cover layer and the plurality of sensing elements is between 0.2 and 2.0 mm.

8. The optical sensor according to claim 1, wherein the plurality of diffractive optical elements of the optical layer are configured to generate constructive interference of light at the plurality of sensing elements.

9. An optical fingerprint sensor for imaging a fingerprint, wherein the optical fingerprint sensor comprises:
  a cover layer transparent to light reflected off the fingerprint;
  an optical layer, disposed below the optical layer, having a plurality of diffractive optical elements; and
  a sensing layer, having a plurality of sensing elements disposed below the optical layer, wherein each of the plurality of sensing elements are configured to detect light from the fingerprint;
  wherein each of the plurality of diffractive optical elements of the optical layer is configured to diffract and direct light from the fingerprint to one or more of the plurality of sensing elements; and
  wherein the plurality of diffractive optical elements comprises one or more binary zone plates.

10. The optical fingerprint sensor according to claim 9, wherein each of the plurality of diffractive optical elements of the optical layer is configured such that light passing through the respective diffractive optical element is resolvable at only one sensing element of the plurality of sensing elements.

11. The optical fingerprint sensor according to claim 9, wherein each of the plurality of diffractive optical elements of the optical layer is configured such that light passing through the respective diffractive optical element is resolvable at multiple sensing elements of the plurality of sensing elements.

12. A system for imaging a biometric object, the system comprising:
  an optical sensor, comprising:
    a cover layer transparent to light reflected off the biometric object;
    an optical layer, disposed below the cover layer, having a plurality of diffractive optical elements; and
    a sensing layer, having a plurality of sensing elements disposed below the optical layer;
    wherein each of the plurality of diffractive optical elements of the optical layer is configured to diffract and direct light from the biometric object to the plurality of sensing elements, and wherein the plurality of diffractive optical elements comprises one or more binary zone plates; and
  a processing system, connected to the plurality of sensing elements, configured to obtain image data from the plurality of sensing elements and compare the obtained image data to a reference template.

13. The system according to claim 12, wherein the processing system is further configured to combine partial images corresponding to the image data into composite data before comparing the obtained image data to a reference template.

14. The system according to claim 12, wherein the processing system is further configured to, based on comparing the obtained image data to a reference template, to output an authentication result.

15. The system according to claim 12, wherein each of the plurality of diffractive optical elements of the optical layer is configured such that light passing through the respective diffractive optical element is resolvable at only one sensing element of the plurality of sensing elements.

16. The system according to claim 12, wherein each of the plurality of diffractive optical elements of the optical layer is configured such that light passing through the respective diffractive optical element is resolvable at multiple sensing elements of the plurality of sensing elements.

17. An optical sensor for imaging a biometric object, the optical sensor comprising:

a cover layer transparent to light reflected off the biometric object;

an optical layer, disposed below the cover layer, having a plurality of diffractive optical elements; and a sensing layer, having a plurality of sensing elements disposed below the optical layer, each of the sensing elements being configured to detect light from the biometric object;

wherein each of the plurality of diffractive optical elements of the optical layer is configured to diffract and direct light from the biometric object to one or more of the plurality of sensing elements;

wherein the plurality of diffractive optical elements comprises one or more photon sieves.

18. The optical sensor according to claim 17, wherein each of the plurality of diffractive optical elements of the optical layer is configured such that light passing through the respective diffractive optical element is resolvable at only one sensing element of the plurality of sensing elements.

19. The optical sensor according to claim 17, wherein each of the plurality of diffractive optical elements of the optical layer is configured such that light passing through the respective diffractive optical element is resolvable at multiple sensing elements of the plurality of sensing elements.

20. The optical sensor according to claim 17, wherein the optical layer comprises an opaque substrate with openings.

21. The optical sensor according to claim 17, further comprising:

a light source, configured to provide the light which is reflected off the biometric object.

22. The optical sensor according to claim 17, wherein the biometric object is a fingerprint, and each of the plurality of diffractive optical elements corresponds to a respective subview or pixel of the fingerprint.

23. The optical sensor according to claim 17, wherein the distance between a top surface of the cover layer and the plurality of sensing elements is between 0.2 and 2.0 mm.

24. The optical sensor according to claim 17, wherein the plurality of diffractive optical elements of the optical layer are configured to generate constructive interference of light at the plurality of sensing elements.

* * * * *